US008053609B2

(12) United States Patent
Crudge et al.

(10) Patent No.: US 8,053,609 B2
(45) Date of Patent: Nov. 8, 2011

(54) SOLID CATALYST USEFUL FOR CONVERTING AN ALKYLENE OXIDE TO AN ALKYLENE GLYCOL

(75) Inventors: William Crudge, Upper Saddle River, NJ (US); Jaap Willem van Hal, Fresno, TX (US); Xiankuan Zhang, Houston, TX (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 0 days.

(21) Appl. No.: 11/872,318

(22) Filed: Oct. 15, 2007

(65) Prior Publication Data
US 2009/0099393 A1 Apr. 16, 2009

(51) Int. Cl.
*C07C 27/00* (2006.01)

(52) U.S. Cl. ......... 568/867; 568/727; 568/728; 502/159

(58) Field of Classification Search .......... 568/867, 568/727, 728; 502/159
See application file for complete search history.

(56) References Cited

U.S. PATENT DOCUMENTS 6,156,942 A * 12/2000 Lemanski et al. ............ 568/867
6,730,816 B2 * 5/2004 Lundquist .................... 568/727

FOREIGN PATENT DOCUMENTS

| EP | 0156449 | 10/1985 |
|----|---------|---------|
| JP | 57139026 | 8/1982 |
| SU | 2001901 C1 | 5/1992 |
| SU | 2002726 | 5/1992 |
| WO | WO9520559 | 8/1995 |
| WO | WO9733850 | 9/1997 |

OTHER PUBLICATIONS

Aldrich Catalog, 1992-1993; Catalog # 247669.*
Aldrich Catalog, 1991-1993, Product detail for catalog No. 247669.*

* cited by examiner

*Primary Examiner* — Elvis O Price
(74) *Attorney, Agent, or Firm* — Scully, Scott, Murphy & Presser, P.C.

(57) ABSTRACT

A solid (i.e., heterogeneous) catalyst useful for preparing an alkylene glycol from the corresponding alkylene oxide as well as a process for the catalytic hydration of an alkylene oxide to an alkylene glycol utilizing such a catalyst are provided. The catalyst of the present invention is based on an ion exchange resin including polystyrene crosslinked with from about 2 to about 10 weight (wt.) % divinyl benzene. The ion exchange resin further includes quaternary ammonium groups or quaternary phosphonium groups. The process includes reacting water and an alkylene oxide in at least one reactor under conditions to form an alkylene glycol, wherein the at least one reactor includes a catalyst based on an ion exchange resin that includes polystyrene crosslinked with from about 2 to about 10 weight (wt.) % divinyl benzene.

15 Claims, No Drawings

US 8,053,609 B2

SOLID CATALYST USEFUL FOR CONVERTING AN ALKYLENE OXIDE TO AN ALKYLENE GLYCOL

FIELD OF THE INVENTION

The present invention relates to the catalytic hydration of an alkylene oxide to an alkylene glycol utilizing a solid catalyst that is based on an ion exchange resin. More particularly, the present invention relates to the catalytic hydration of ethylene oxide to ethylene glycol utilizing a catalyst that is based on an ion exchange resin having polystyrene crosslinked with a specific amount of divinyl benzene.

BACKGROUND OF THE INVENTION

Alkylene glycols, such as monoalkylene glycols, are of continued commercial interest and the demand for the same has increased. For example, monoalkylene glycols are used in anti-freeze compositions, as solvents and as base materials in the production of polyalkylene terephthalates, e.g., for fibers and bottles.

Alkylene glycols are typically prepared from their corresponding alkylene oxide utilizing a liquid phase hydrolysis process. In commercial production, the hydrolysis reaction is performed without a catalyst by adding a large excess of water, e.g., 15 to 30 moles of water per mole of alkylene oxide. The prior art hydrolysis reaction is a nucleophilic substitution reaction, in which ring opening of the alkylene oxide occurs and water serves as the nucleophile.

Because initially formed monoalkylene glycol also acts as a nucleophile, a mixture of monoalkylene glycol, dialkylene glycol and higher alkylene glycols is typically formed. In order to increase the selectivity to monoalkylene glycol, it is necessary to suppress the secondary reaction between the primary product and the alkylene oxide, which competes with the hydrolysis of the alkylene oxide.

One effective technique for suppressing the secondary reaction is to increase the amount of water present in the reaction mixture. Although this prior art technique improves the selectivity towards the production of the monoalkylene glycol, it creates a problem in that large amounts of water have to be removed. Removing such additional water increases production costs because such a removal process is energy intensive and requires large-scale evaporation/distillation facilities.

A number of prior art publications show that higher selectivity to monoalkylene glycols can be achieved if the reactions are conducted using heterogeneous catalytic processes, such as, for example, with catalysts based on an ion exchange resin as disclosed in EP-A-156,449 (metalate-containing anion exchange resins); JP-A-57-139026 (anion-exchange resin in the halogen form); Russian Patent Nos. 2062726 and 2001901 (anion exchange resin in the bicarbonate form); WO 95/20559 (anion exchange resin); and WO 97/33850 (anion exchange resin).

Despite all of the advances made in the catalytic hydrolysis of alkylene oxides, there is a continued need for providing a new and improved catalytic hydration (e.g., hydrolysis) process for producing monoalkylene glycol from the corresponding alkylene oxides. In particular, there is a need for providing a solid (i.e., heterogeneous) catalyst that is used in such catalytic hydration reactions such that the heterogeneous catalyst employed provides improved conversion and/or selectivity.

SUMMARY OF THE INVENTION

In view of the above, the present invention provides an improved solid (i.e., heterogeneous) catalyst useful for preparing an alkylene glycol from the corresponding alkylene oxide as well as a process for the catalytic hydration of an alkylene oxide to an alkylene glycol utilizing such a catalyst.

Specifically, the catalyst of the present invention comprises an ion exchange resin including polystyrene crosslinked with from about 2 to about 10 weight (wt.) % divinyl benzene.

In an embodiment of the present invention, the ion exchange resin includes polystyrene that is crosslinked with from about 4 to about 8 wt. % divinyl benzene.

The ion exchange resin typically includes basic groups that are bonded to the crosslinked polystyrene resin. The basic groups which are bonded to the crosslinked polystyrene resin include quaternary ammonium or quaternary phosphonium, with quaternary ammonium groups preferred.

The ion exchange resin of the present invention is typically a strongly basic (i.e., anionic) ion exchange region which includes at least one anion. Preferably, the anion is selected from the group of bicarbonate, bisulfite, metalate, halide, hydroxide and carboxylate anions, with a bicarbonate anion being highly preferred.

Applicants have determined that a catalyst based on an ion exchange resin including polystyrene that is crosslinked with from about 2 to about 10, preferably from about 4 to about 8, wt. % divinyl benzene exhibits improved catalytic hydration properties such as, for example, improved conversion of an alkylene oxide, especially ethylene oxide, and/or improved selectivity to an alkylene glycol, especially monoethylene glycol of said hydration reaction as compared to a catalyst of the same type wherein the content of divinyl benzene is above and/or below the range mentioned above.

Because of the degree of divinyl benzene crosslinking present in the ion exchange resin, a balance is maintained between the water absorbing capacity of the resin and the elastic forces of the copolymer to keep the swollen resin in a stable moisture content. Typically, the ion exchange resin employed in the present invention has a water retention value that is from about 35 to about 80%, with a water retention value from about 40 to about 65% being even more typical. In ion exchange resins with a higher divinyl benzene crosslinkage, the chains of the polymeric matrix cannot elongate as much so these resins hold less water due to the limited swelling ability. Resins with a lower divinyl benzene crosslinkage can hold more water since they can swell more.

The ion exchange resin employed in the present invention is transparent and has a gel structure, hence it may also be referred to as a 'gel type' ion exchange resin. Moreover, the ion exchange resin that is employed in the present invention has an exchange capacity from about 0.75 to about 3.4 eq/L, with an exchange capacity from about 0.8 to about 1.5 eq./L being highly preferred. The exchange capacity of an ion exchange material is equal to the number of fixed ionic sites that are capable of entering into an ion exchange reaction.

In some embodiments, the ion exchange resin employed in the present invention includes a quaternary ammonium functionality (i.e., group) which may include three methyl groups attached to the nitrogen atom of the quaternary ammonium functionality, or two methyl groups and one ethyl alcohol group attached to the nitrogen atom of the quaternary ammonium functionality. In some embodiments of the present invention, it is preferred to utilize an ion exchange resin in which three methyl groups are attached to the nitrogen atom of the quaternary ammonium functionality, which may also be referred to as a "Type I" anion exchange resin.

In another embodiment of the present invention, it is preferred that the ion exchange resin employed in the present invention has an average bead size of greater than 0.2 mm to less than 1.5 mm. It is noted that the bead sizes mentioned herein are averaged bead sizes unless stated to the contrary. In some instances, neither large beads (greater than or equal to 1.5 mm) nor small beads (i.e., less than or equal to 0.2 mm) are as effective.

In another aspect, the present invention provides a catalytic hydrolysis process of converting an alkylene oxide, preferably ethylene oxide, into its corresponding alkylene glycol, preferably monoethylene glycol. The inventive method comprises:

reacting water and an alkylene oxide in at least one reactor under conditions to form an alkylene glycol, wherein said at least one reactor includes a catalyst based on an ion exchange resin, said ion exchange resin including polystyrene crosslinked with from about 2 to about 10 weight (wt.) % divinyl benzene.

DETAILED DESCRIPTION OF THE INVENTION

The present invention, which provides a solid catalyst based on an ion exchange resin that is useful in a catalytic hydration (i.e., hydrolysis) process for producing an alkylene glycol from an alkylene oxide, particularly, monoethylene glycol from ethylene oxide, as well as a catalytic hydration process that employs the inventive solid catalyst, will now be described in greater detail by referring to the following discussion.

As stated above, the present invention provides a catalytic hydrolysis process for preparing an alkylene glycol by reacting alkylene oxide and water in the presence of a solid catalyst that is based on an ion exchange resin. The solid catalyst that is based on the ion exchange resin will be described in greater detail herein below.

The term "alkylene" is used in the present invention to denote an organic functional group formed from an unsaturated aliphatic hydrocarbon typically having from 2 to 22 carbon atoms, preferably 2 to 6 carbon atoms. The preferred alkylene oxides that are employed in the present invention include ethylene oxide (EO), propylene oxide (PO), and butylene oxide (BO). The preferred alkylene glycols include their respective monoalkylene glycols: monoethylene glycol (MEG), monopropylene glycol (MPG), and monobutylene glycol (MBG). Most preferably, the present invention provides a method for preparing MEG from ethylene oxide and water.

The hydrolysis reaction employed in the present invention is performed in any type of reactor (or combination of reactors) including, for example, an adiabatic reactor and/or a non-adiabatic reactor. By "adiabatic" it is meant that no substantial transfer of heat occurs to, or from, the reactor system. Thus, the reactor systems employed in some embodiments of the present invention include at least one means for removing/transferring heat to and from the system. Such means for removing/transferring heat are well known to those skilled in the art. In one embodiment of the present invention, the reactor includes a heating/cooling jacket that is wrapped around the outside of the reactor.

In some embodiments of the present invention, the reaction mixture (i.e., reactants: water and alkylene oxide) is fed to the bottom of the reactor. The reaction mixture then flows upward through the catalyst bed, where it reacts and forms glycol product, then immediately exits the reactor. Such a process is referred to as an upflow process. When an upflow operation is performed within the reactor, the upflow operation is achieved by feeding liquid into the bottom of the reactor and removing liquid as well as catalyst particles from the top of the reactor.

In other embodiments of the present invention, the reaction mixture (i.e., reactants: water and alkylene oxide) is fed to the top of the reactor. The reaction mixture then flows downward through the catalyst bed, where it reacts and forms glycol product, then immediately exits the reactor. Such a process is referred to as a downflow process.

In the present invention, at least one of the reactors employed in a series must contain a catalyst bed comprising a heterogeneous catalyst based on an ion exchange resin that is capable of performing a hydrolysis reaction.

The water that is employed in the present invention may be of different purity. Examples of types of water that can be used as one of the hydrolysis reactants include: deionized water, steam distilled water, condensate water (which may contain some residual glycol compounds), and also recycled water recovered from the dehydration process in the production of alkylene oxide and alkylene glycol (which may contain residual glycols).

Water is provided in an amount which is in a stoichiometric excess of that required for forming a desired glycol from reaction with alkylene oxide. Preferably, the molar feed ratio of water to alkylene oxide is at least about 1.1, more preferably at least about 2.0, and even more preferably at least about 5.0. Preferably, the molar feed ratio is no more than about 30, more preferably no more than about 25, and even more preferably no more than about 20. One skilled in the art will recognize that this ratio will vary depending upon the alkylene oxide employed, the reaction conditions, and the specific catalyst utilized.

The water and alkylene oxide feed may be fed to the first reactor separately or together as a co-feed. Preferably, water and alkylene are co-fed into the first reactor. The water and alkylene oxide are fed to the reactors as a liquid.

The first step of the inventive process comprises feeding water and alkylene oxide into a first reactor under conditions such that the alkylene oxide and water react to form a glycol product stream comprising a glycol and water. For purposes of this invention, the "glycol product stream" denotes any product stream exiting the reactor which contains at least glycol and water. The glycol product is generally in mixture, solution, or contained within unreacted water.

Conditions which are conducive for the reaction to occur are well known to those skilled in the art and may vary depending on the type of catalysts used as well as the type of reactor used. Factors for consideration include the optimum temperature, pressure, and water to alkylene oxide ratio for reacting the feed stream(s) without providing conditions, which significantly degrade the catalyst bed or selectivity to the desired product.

The reaction temperature in reactors containing the catalyst bed is from about 30° C. to about 160° C., and preferably from about 50° C. to about 150° C. When a temperature sensitive ion exchange resin is employed, it has been determined that the lifetime of the resin is sufficiently maintained when the temperature of the reaction is kept below 100° C.; a temperature sensitive ion exchange resin can still be employed when the temperature is greater than 100° C. but the lifetime of such a resin may be reduced when operating at higher temperatures. The reaction pressure may vary depending on the reaction temperature employed as well as the composition that is fed into the reactor. The pressure is however high enough to avoid vapor formation. The selection of an appropriate reaction pressure is within the knowledge of one skilled in the art.

As set forth hereinabove, a catalyst bed must be included in at least one of the reactors in series. Typically, but not necessarily always, the catalyst bed is a fixed catalyst bed which can become fluidized or expand under operation. The catalyst bed comprises an ion exchange resin (to be defined in greater detail herein below) that is capable of catalyzing the desired reaction in the reactor in which it is employed. The ion exchange resin should be of such a nature as to allow reactants and products to pass through the bed. Desirably, the ion exchange resin is solid and is insoluble in either the reactants or the glycol products under the conditions in the process.

The catalyst employed in the present invention is based on an ion exchange resin having a copolymer of styrene and divinyl benzene, wherein divinyl benzene is present in amount from about 2 to about 10 wt. %. That is, the ion exchange resin employed in the inventive hydrolysis catalyst includes polystyrene that is crosslinked with from about 2 to about 10 wt. % divinyl benzene. In a preferred embodiment, the catalyst includes polystyrene that is crosslinked with from about 4 to about 8 wt. % divinyl benzene.

The ion exchange resin employed in the present invention typically includes basic groups that are bonded to the crosslinked polystyrene resin. The basic groups which are bonded to the crosslinked polystyrene resin include quaternary ammonium or quaternary phosphonium, with quaternary ammonium groups being preferred.

The ion exchange resin employed in the present invention typically includes more than one anion. Preferably, the anion is selected from the group of bicarbonate, bisulfite, metalate, halide, hydroxide and carboxylate anions, with a bicarbonate anion being highly preferred. When the anion is a carboxylate anion, it is preferred that the anion is a polycarboxylic acid anion having in its chain molecule one or more carboxyl groups and one or more carboxylate groups, the individual carboxyl and/or carboxylate groups being separated from each other in the chain molecule by a separating group consisting of at least one atom. Preferably the polycarboxylic acid anion is a citric acid derivative, more preferably a mono-anion of citric acid. Most preferably the anion is a bicarbonate anion.

A solid catalyst which has given particularly good results when employed in the process of the present invention, is a catalyst based on a quaternary ammonium resin, preferably a resin comprising a trimethylbenzyl ammonium group, and wherein the anion is a bicarbonate anion.

Applicants have determined that a catalyst based on an ion exchange resin including polystyrene that is crosslinked with from about 2 to about 10 wt. % divinyl benzene exhibits improved catalytic hydration properties such as, for example, improved conversion of an alkylene oxide, especially ethylene oxide, and/or improved selectivity to an alkylene glycol, especially monoethylene glycol of said hydration reaction as compared to a catalyst of the same type wherein the content of divinyl benzene is above and/or below the range mentioned above.

Because of the degree of divinyl benzene crosslinking present in the ion exchange resin, a balance is maintained between the water absorbing capacity of the resin and the elastic forces of the copolymer to keep the swollen resin in a stable moisture content. Typically, the ion exchange resin employed in the present invention has a water retention value that is from about 30 to about 80%, with a water retention value from about 40 to about 65% being even more typical.

In ion exchange resins with a higher divinyl benzene crosslinkage, the chains of the polymeric matrix cannot elongate as much so these resins hold less water due to the limited swelling ability. Resins with a lower divinyl benzene crosslinkage can hold more water since they can swell more.

The exchange resin employed in the present invention is transparent and has a gel structure. Moreover, the ion exchange resin that is employed in the present invention has an exchange capacity from about 0.75 to about 3.4 eq/L, with an exchange capacity from about 0.8 to about 1.5 eq./L being highly preferred.

In some embodiments, the ion exchange resin employed in the present invention also includes a quaternary ammonium functionality (i.e., group) which may include three methyl groups attached to the nitrogen atom of the quaternary ammonium functionality, or two methyl groups and one ethyl alcohol group attached to the nitrogen atom of the quaternary ammonium functionality. In some embodiments, of the present invention, it is preferred to utilize an ion exchange resin in which three methyl groups are attached to the nitrogen atom of the quaternary ammonium functionality, which may also be referred to as a "Type I" anion exchange resin.

In another embodiment of the present invention, it is preferred that the ion exchange resin employed in the present invention has an average bead size of greater than 0.2 mm to less than 1.5 mm. In some instances, neither large beads (greater than or equal to 1.5 mm) nor small beads (i.e., less than or equal to 0.2 mm) are as effective.

The catalyst employed in the present invention which is based upon the above mentioned ion exchange resin can be purchased from a suitable resin manufacturer or it can be formed utilizing conventional techniques well known in the art. For example, the catalyst can be formed by first mixing styrene, which has one vinyl group, with divinyl benzene, which has two vinyl groups. The divinyl benzene (DVB) is present in the mixture in an amount from about 2 to about 10 wt. %, the remainder of the mixture includes styrene. Polymerization is then initiated utilizing conventional techniques that are well known to those skilled in the art. Typically, but not necessarily always, the polymerization is performed in the presence of a protic solvent such as water. After polymerization, the ion exchange resin is manufactured by introducing basic functionalities, such as for example, quaternary ammonium or quaternary phosphonium onto the resultant copolymer matrix utilizing conventional chemical reactions which are well known to those skilled in the art.

The hydrolysis reaction may be conducted in the presence of carbon dioxide. Whether to provide carbon dioxide to the reaction may depend on whether a catalyst is utilized in the reactor and the type of catalyst used. The carbon dioxide may be provided to the reaction in any convenient manner. The carbon dioxide may, for instance, be introduced separately and/or with one or more of the feed streams. The carbon dioxide may be present in the reaction mixture in gaseous form or in the form of carbonic acid or in the form of salts of carbonic acid. Preferably, the carbon dioxide is present in the reaction mixture in an amount less than, or equal to, 0.1 wt %, preferably 0.05 wt %, more preferably 0.01 wt %.

The reaction of this invention may also be conducted in the presence of a pH adjusting additive. Whether to provide a pH adjusting additive to the reaction may be driven by factors such as the type of catalyst used, and whether carbon dioxide is fed to the catalyst bed. For example, if the bicarbonate form of an anion exchange resin is utilized as a catalyst, it may be desirable to provide an amount of pH adjusting additive to the catalyst bed. Such additives typically comprise any organic or inorganic bases such as alkylamines, pyridine, alkali phosphates, alkali sulphates, alkali carbonates, alkali metal hydroxide, and combinations thereof. "Bases", as used herein, shall be defined as compounds that, when added to water, give a pH of greater than 7.0. Preferably, the pH adjusting additive comprises sodium hydroxide (NaOH). The pH adjusting additive is provided in an amount sufficient to maintain a pH of the reaction mixture at a lower limit of about 5.0, more preferably 5.5, and most preferably 6.0. For an upper pH limit, the pH adjusting additive is provided in an amount sufficient to maintain a pH of the reaction mixture below about 9.0, preferably 8.0, and more preferably 7.0. By referring to "pH of the reaction mixture" it is meant the pH of the mixture which includes each of the components which are fed to the reactor.

The following examples are provided to illustrate the present invention and to demonstrate some advantages that can be achieved when using the same.

In the examples that follow, the ion exchange resins employed are crosslinked copolymers of styrene and divinylbenzene (DVB). The crosslinked copolymers were purchased from a suitable resin manufacturer, and were then subjected to conventional ion exchanging techniques. Examples of some resins manufacturers include Rohm & Haas, Dow, Lanxess (formerly Bayer), Purolite, Mitsubishi and Thermax.

Each of the ion exchange resins used in the examples below is a type I strong base anion exchange resin (gel type) that is in bicarbonate form.

In the examples, the amount of DVB used in the co-polymerization determines the crosslinking in the final ion exchange resin. This is expressed as the proportion of DVB in % [(weight of DVB)/(weight of total monomers)×100]. DVB causes chain branching during the polymerization forming a fine mesh structure with chain branching. Increasing the amount of DVB increases the amount of fine mesh and chain branching in the ion exchange resin.

EXAMPLE 1

The catalysts (15 ml) were tested at 100° C. (jacket temperature) in a plug flow tube reactor with a feed having 8:1 weight ratio of water to ethylene oxide at a flow rate of 2.0 ml/min in an up flow mode and the data shown in Table 1 below were taken after 80 hours on stream.

TABLE 1

| Catalyst | DVB Crosslinkage | Conversion (%) | Selectivity (%) |
| --- | --- | --- | --- |
| Catalyst A | 2% | 96.8 | 95.8 |
| Catalyst B | 7% | 98.4 | 98.4 |
| Catalyst C | 7% | 98.9 | 97.7 |

The data in the above table illustrates that the inventive resin-based catalysts are active and selective.

EXAMPLE 2

The catalysts (15 ml) were tested at 100° C. (jacket temperature) in a plug flow tube reactor with a feed having 8:1 weight ratio of water to ethylene oxide at a flow rate of 1.5 ml/min in an up flow mode and the data shown in Table 2 below were taken after 80 hours on stream.

TABLE 2

| Catalyst | DVB Crosslinkage | Conversion (%) | Selectivity (%) |
| --- | --- | --- | --- |
| Catalyst D | 2% | 99.3 | 88.8 |
| Catalyst E | 4% | 99.7 | 98.3 |
| Catalyst F | 8% | 99.9 | 98.4 |

The data in the above table illustrates that the inventive resin-based catalysts are active and selective.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed as new is:

1. A process of preparing an alkylene glycol, the process comprising:
   reacting water and an alkylene oxide in at least one reactor under conditions to form an alkylene glycol, wherein said at least one reactor includes a catalyst consisting essentially of a strongly basic ion exchange resin that includes polystyrene crosslinked with from about 2 to about 10 wt. % divinyl benzene, wherein said resin has an average bead size of greater than 0.2 mm to less than 1.5 mm.

2. The process of claim 1 wherein said strongly basic ion exchange resin includes quaternary ammonium groups or quaternary phosphonium groups.

3. The process of claim 1 wherein said strongly basic ion exchange resin includes a catalyst anion, said catalyst anion is one of bicarbonate, carboxylate, bisulphate, halide, hydroxide and a metallate anion.

4. The process of claim 1 wherein said strongly basic ion exchange resin includes quaternary ammonium groups having three methyl groups bonded to a nitrogen atom of each quaternary ammonium group.

5. The process of claim 1 wherein said strongly basic ion exchange resin includes quaternary ammonium groups having two methyl groups and one ethyl alcohol group bonded to a nitrogen atom of each quaternary ammonium group.

6. The process of claim 1 wherein said water is present in a molar feed ratio of water to alkylene oxide of at least about 1.1, but not more than 30.

7. The process of claim 1 wherein said alkylene oxide is ethylene oxide (EO), propylene oxide (PO) or butylene oxide (BO).

8. The process of claim 1 wherein said alkylene glycol is monoethylene glycol (MEG), monopropylene glycol (MPG) or monobutylene glycol (MBG).

9. The process of claim 1 wherein said alkylene oxide is ethylene oxide and said alkylene glycol is monoethylene glycol.

10. The process of claim 1 wherein said reacting is performed at a temperature from about 30° C. to about 160° C.

11. The process of claim 1 wherein said water and said alkylene oxide are added from a top of said at least one reactor and flow downward into a bed including said catalyst.

12. The process of claim 1 wherein said reacting occurs in the presence of carbon dioxide.

13. The process of claim 1 wherein said reacting occurs at a temperature below 100° C.

14. The process of claim 1 wherein said strongly basic ion exchange resin includes polystyrene crosslinked with 2 wt. % divinyl benzene, 4 wt. % divinyl benzene or 7 wt. % divinyl benzene.

15. A process of preparing an alkylene glycol, the process comprising:
   reacting water and an alkylene oxide in at least one reactor under conditions to form an alkylene glycol, wherein said at least one reactor includes a catalyst consisting essentially of a strongly basic ion exchange resin that includes polystyrene crosslinked with from about 2 up to about 7 wt. % divinyl benzene.

* * * * *